US012685676B2

(12) United States Patent
Giansante

(10) Patent No.: US 12,685,676 B2
(45) Date of Patent: Jul. 21, 2026

(54) METHOD AND APPARATUS FOR FOLDING ABSORBENT SANITARY ARTICLES

(71) Applicant: Fameccanica.Data S.p.A., San Giovanni Teatino Chieti (IT)

(72) Inventor: Antonio Giansante, San Giovanni Teatino Chieti (IT)

(73) Assignee: Fameccanica.Data S.p.A., San Giovanni Teatino Chieti (IT)

( * ) Notice: Subject to any disclaimer, the term of this patent is extended or adjusted under 35 U.S.C. 154(b) by 24 days.

(21) Appl. No.: 18/916,867

(22) Filed: Oct. 16, 2024

(65) Prior Publication Data

US 2025/0127662 A1 Apr. 24, 2025

(30) Foreign Application Priority Data

Oct. 18, 2023 (IT) ........................ 102023000021702

(51) Int. Cl.
*A61F 13/15* (2006.01)
*B65H 45/16* (2006.01)
(52) U.S. Cl.
CPC .. *A61F 13/15747* (2013.01); *A61F 13/15764* (2013.01); *A61F 13/15804* (2013.01)
(58) Field of Classification Search
CPC .................................................... B65H 45/16
USPC ........................... 53/429, 116; 493/423, 441
See application file for complete search history.

(56) References Cited

U.S. PATENT DOCUMENTS

| | | | | |
|---|---|---|---|---|
| 8,439,814 B2 * | 5/2013 | Piantoni | ................ | B65H 45/16 |
| | | | | 493/422 |
| 8,672,824 B2 * | 3/2014 | Sablone | ............ | A61F 13/15764 |
| | | | | 493/441 |
| 10,167,156 B2 * | 1/2019 | Ingole | .................... | B65H 20/12 |
| 2008/0223537 A1 | 9/2008 | Wiedmann | | |
| 2015/0374555 A1 * | 12/2015 | Chen | ................ | A61F 13/15747 |
| | | | | 493/422 |

FOREIGN PATENT DOCUMENTS

| | | | | |
|---|---|---|---|---|
| EP | 2157952 A1 | 3/2010 | | |
| EP | 4420644 A1 | 8/2024 | | |
| WO | WO-2013136252 A2 * | 9/2013 | ............ | B65D 85/07 |

OTHER PUBLICATIONS

Search Report dated Apr. 22, 2024. 7 pages.
European Search Report dated Feb. 21, 2025. 6 pages.

* cited by examiner

*Primary Examiner* — Shelley M Self
*Assistant Examiner* — Patrick B Fry
(74) *Attorney, Agent, or Firm* — RMCK Law Group PLC

(57) ABSTRACT

A method for folding absorbent sanitary articles, wherein a plurality of absorbent sanitary articles advancing at a first speed are alternately routed towards at least two folding lines, are slowed down to a second speed less than the first speed, are folded while advancing at the second speed, and are fed aligned with each other in a common outlet array.

10 Claims, 3 Drawing Sheets

METHOD AND APPARATUS FOR FOLDING ABSORBENT SANITARY ARTICLES

CROSS-REFERENCE TO RELATED APPLICATION

This application claims priority to Italian Patent Application No. 102023000021702 filed Oct. 18, 2023. The disclosure of the above application is incorporated herein by reference in its entirety.

FIELD OF THE INVENTION

The present invention relates in general to the packaging of absorbent sanitary articles.

In particular, the invention refers to folding absorbent sanitary articles around one or two transverse folding lines at the end of a production line and upstream of a packaging machine.

The invention was developed in particular with a view to its application to the field of female sanitary napkins, such as for example panty liners, light inco, or the like.

The invention, however, is not limited to this specific field and can be used in all cases where there is a need to fold absorbent sanitary articles around one or two transverse folding lines.

DESCRIPTION OF THE PRIOR ART

Some absorbent sanitary articles, such as female sanitary pads, are often individually packaged in their own pouch-like packaging.

The individual packaging of absorbent sanitary articles may be carried out by enclosing the individual absorbent sanitary articles between two flexible sheets superimposed on each other which enclose a respective absorbent sanitary article in the manner of a sandwich and joined together at their edges by adhesive.

Solutions are also known wherein each absorbent sanitary article is closed in a casing made up of a single sheet of flexible material folded to form two flaps joined together at their edges by adhesive.

The packages may be made up of sheets of plastic material, for example, polyethylene, or paper material.

Before packaging, absorbent sanitary articles are often folded into two or three. This folding is carried out by folding the absorbent sanitary articles around one or two transverse axes with respect to a longitudinal axis of the article. Female sanitary pads are often folded into three overlapping parts.

EP-A-2157952, FIG. 18, describes an apparatus for folding disposable absorbent articles into three, wherein the absorbent articles are inserted between two opposing belts by folding blades which impact the articles transversally along fold lines. In a first folding assembly, the sanitary articles are folded for approximately one third of their length. The partially folded articles are sent to a second folding assembly which folds the remaining part, producing a tri-folded sanitary article made up of three overlapping layers.

In modern machines for producing absorbent sanitary articles, the articles move at extremely high speeds. For example, in the case of absorbent sanitary articles with a length in the machine direction of 300 mm and with a machine operating at a rate of 1000 pieces per minute, the articles move at a speed of 300 m/min and each of the folding blades impacts the sanitary articles with a frequency of 1000 strokes per minute.

Due to the high linear speed of absorbent sanitary articles upon impact with the folding blades, there is a risk of damage to the articles. The frequency of damage to the absorbent sanitary articles is greater the higher the speed of advancement of the articles.

Typically, the speed of the folding machines is a bottle-neck that limits the speed of the packaging machines. In practice, even if the packaging machines could operate at higher speeds, their speed is limited by the maximum speed of the folding devices.

OBJECT AND SUMMARY OF THE INVENTION

The object of the present invention is to provide a method and an apparatus for folding absorbent sanitary articles that overcome the problems of the prior art.

According to the present invention, this object is achieved, by a method and by an apparatus for folding absorbent sanitary articles having the characteristics forming the subject of claims 1 and 7.

Preferred embodiments form the subject of the dependent claims.

The claims form an integral part of the disclosure provided here in relation to the invention.

BRIEF DESCRIPTION OF THE DRAWINGS

The present invention will now be described in detail with reference to the attached drawings, given purely by way of non-limiting example, wherein.

It will be appreciated that the accompanying drawings are schematic and that—in certain figures—some components may not be shown to assist in understanding the Figures. It will be appreciated that various figures may not be represented on the same scale.

DETAILED DESCRIPTION

Figure 1:
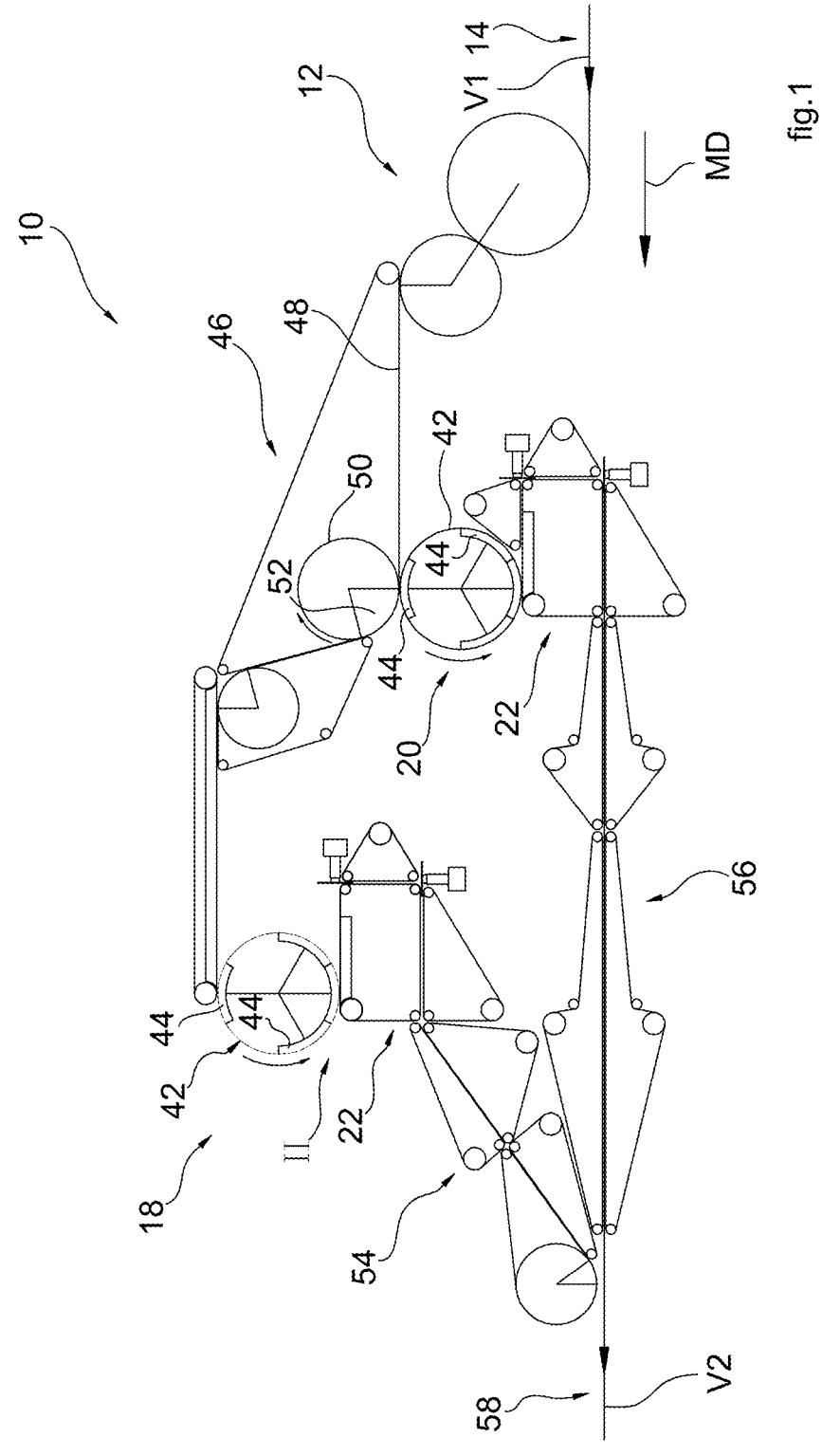
FIG. 1 is a schematic side view of an embodiment of an apparatus for folding absorbent sanitary articles according to the present invention.

With reference to FIG. 1, numeral 10 indicates an apparatus for folding absorbent sanitary articles. The apparatus 10 may be arranged at the outlet of a production machine and upstream of a packaging machine (not shown).

Figures 3A, 3B, 3C, 3D, 3E:
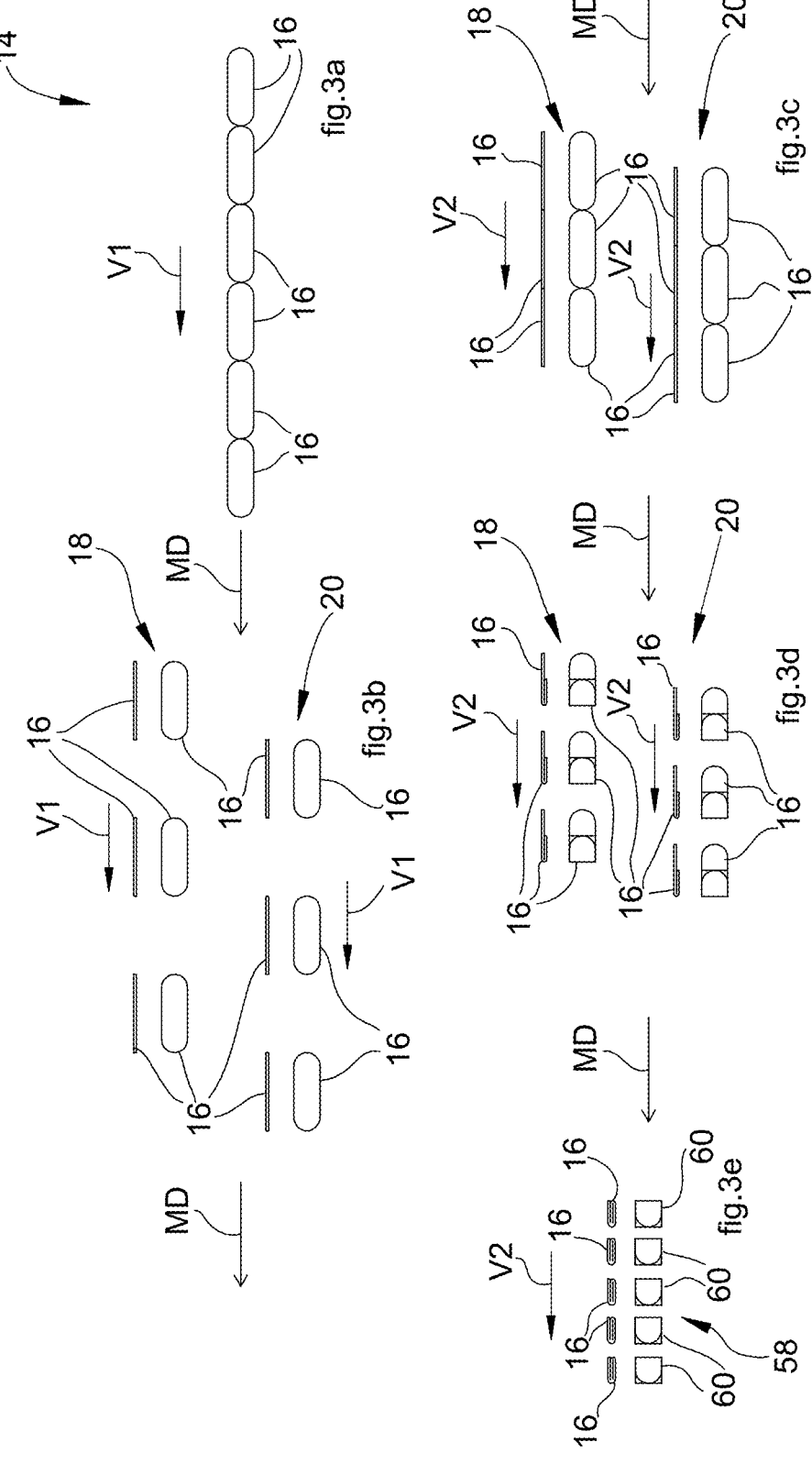

With reference to FIGS. 1 and 3*a*, the apparatus 10 comprises an inlet conveyor 12 configured to advance an inlet array 14 along a machine direction MD at a first speed V1.

The inlet array 14 is formed by a plurality of absorbent sanitary articles 16 aligned with each other. The absorbent sanitary articles 16 forming the inlet array 14 are in the state wherein they leave a production machine. In particular, the absorbent sanitary articles 16 in the inlet array 14 are extended in a flat shape and are package-free.

The absorbent sanitary articles 16 in the inlet array 14 have respective longitudinal axes aligned with each other and parallel to the machine direction MD.

In the inlet array 14 the absorbent sanitary articles 16 may be substantially in contact with each other, so that the pitch between the absorbent sanitary articles 16 is substantially equal to their length.

The apparatus 10 comprises at least two folding lines 18, 20 configured to fold the absorbent sanitary articles 16 around respective transverse axes with respect to the longitudinal axes of the absorbent sanitary articles 16.

In the example illustrated in the figures, the apparatus 10 comprises two folding lines 18, 20. In possible embodiments the apparatus 10 could comprise three or more folding lines.

Each of the folding lines 18, 20 may be configured to fold the absorbent sanitary articles 16 into two or three. When folded into two, the absorbent sanitary articles 16 are folded around a central transversal axis and after folding have two flaps overlapping each other. When folding into three, the absorbent sanitary articles 16 are folded around two transversal axes located approximately at ⅓ and ⅔ of the length of the absorbent sanitary article 16 and after folding they have three flaps overlapping each other.

Figure 2:
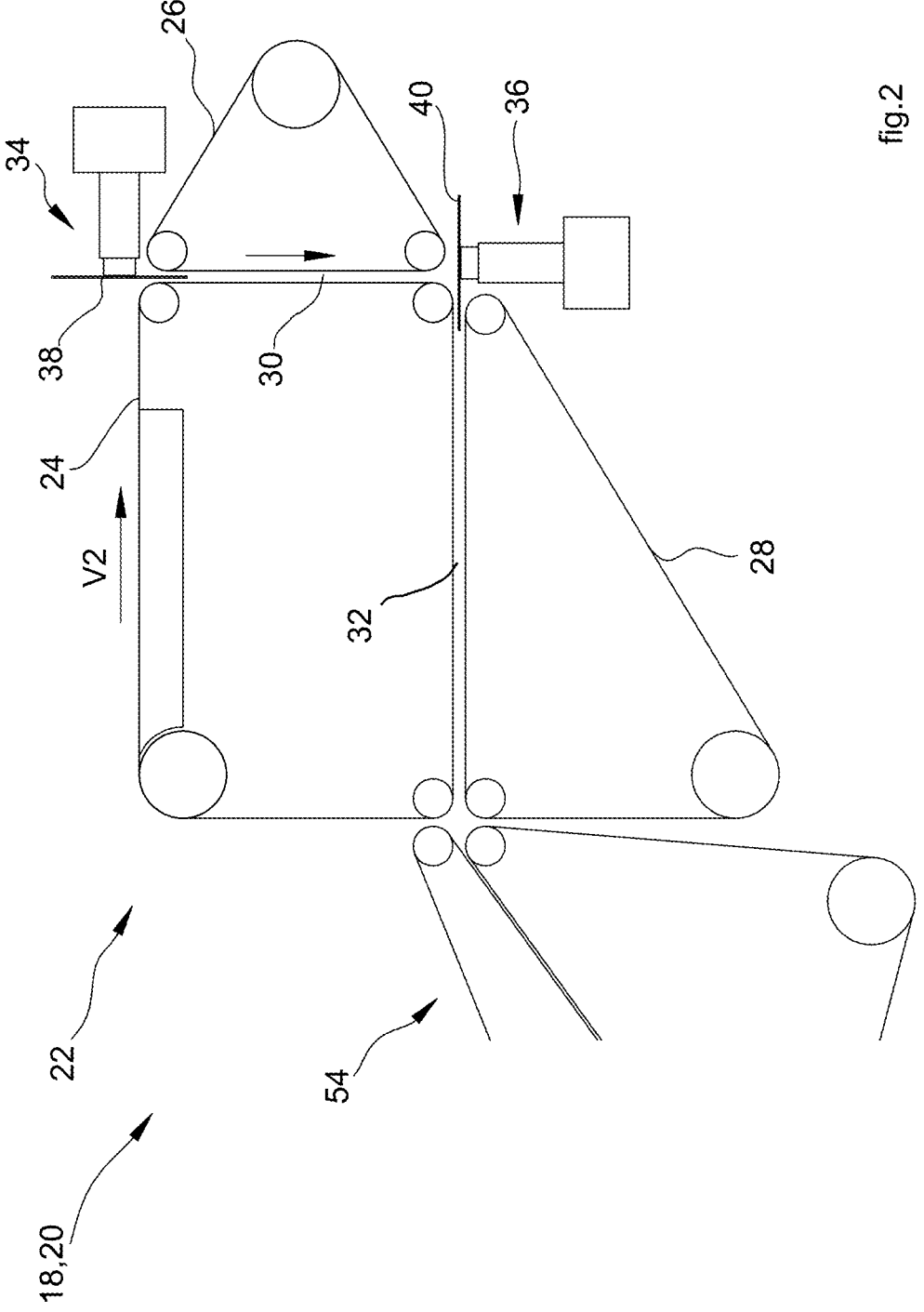
FIG. 2 is a view on an enlarged scale of a folding unit indicated by the arrow II in FIG. 1, and FIGS. 3*a*, 3*b*, 3*c*, 3*d*, 3*e* are schematic views illustrating an embodiment of a method for folding absorbent sanitary articles according to the present invention.

With reference to FIG. 2, each folding line 18, 20 may comprise a belt folding device 22. In the illustrated example, the belt folding device 22 is configured to fold each absorbent sanitary article 16 into three.

The belt folding device 22 comprises a first belt 24, a second belt 26 and a third belt 28. The first belt 24 and the second belt 26 have respective straight sections facing each other, which define a first folding channel 30. The first belt 24 and the third belt 28 have respective straight sections facing each other, which define a second folding channel 32.

The belt folding device 22 comprises a first inserter device 34 configured to insert successive absorbent sanitary articles 16 into the first folding channel 30 and a second inserter device 36 configured to insert successive absorbent sanitary articles 16 into the second folding channel 32. The first and the second inserting devices 34, 36 may have respective rotating folding blades 38, 40. The absorbent sanitary articles 16 move along the belt folding device 22 in the direction indicated by the arrows and are folded transversely a first time in the first folding channel 30 and a second time in the second folding channel 32.

Each of the folding lines 18, 20 comprises a respective slowing device 42 located upstream of the respective belt folding device 22 and configured to slow down the absorbent sanitary articles 16 which are fed to the belt folding device 22 at a second speed V2 less than the first speed V1.

In this way, in each belt folding device 22 the absorbent sanitary articles 16 are folded while advancing at a speed V2 less than the speed V1 at which the absorbent sanitary articles 16 leave the production machine.

The second speed V2 may be equal to V1/n, where n is the number of folding lines 18, 20.

The slowing device 42 may be a rotating repitch device equipped with a plurality of gripping elements 44 which can rotate independently of each other around a common axis. Each of the gripping elements 44 picks up, for example by suction, an absorbent sanitary article 16 advancing at the first speed V1 and releases it to the belt folding device 22 at the second speed V2.

The apparatus 10 comprises a routing device 46 configured to alternatively route the absorbent sanitary articles 16 coming from the inlet array 14 towards the at least two folding lines 18, 20.

In the case wherein the apparatus 10 has two folding lines 18, 20, as in the illustrated example, the routing device 46 routes an absorbent sanitary article 16 towards the first folding line 18 and the immediately successive absorbent sanitary article 16 towards the second folding line 20, and so on, so that each folding line 18 receives half of the absorbent sanitary articles 16 coming from the inlet array 14.

In the case wherein the apparatus 10 has n folding lines, the routing device 46 routes one absorbent sanitary article 16 to each folding line every n, so that each folding line receives 1/n of the absorbent sanitary articles 16 coming from the inlet array 14.

The routing device 46 may comprise a belt having a branch 48 that retains the absorbent sanitary articles 16 by suction, and a transfer wheel 50 provided with one or more suction sectors 52, which alternately transfers the absorbent sanitary articles 16 towards the first folding line 18. The absorbent sanitary items 16 that are not picked up by the transfer wheel 50 are routed to the second folding line 20.

The folding lines 18, 20 comprise respective outlet conveyors 54, 56 which receive the folded absorbent sanitary articles 16 from the respective belt folding device 22 and feed the folded absorbent sanitary articles 16 into a common outlet array 58.

The process of folding into three requires two folds to be carried out on each absorbent sanitary article 16 in series. This may introduce variability in both the dimensions of the folded absorbent sanitary articles 16 in the machine direction MD and the position in the machine direction MD of the folded absorbent sanitary articles 16. This variability must be managed and controlled in order to allow the correct phasing of the products arriving from the two folding lines 18, 20 to obtain a discontinuous chain of folded absorbent sanitary articles 16.

To accomplish this, at least one of the outlet conveyors 54, 56 may be configured to selectively vary the speed of individual folded absorbent sanitary articles 16. A typical device that allows adjustment of the speed of individual folded absorbent sanitary articles 16 is called a "smart belt".

In a start-up step the production machine of (acceleration ramp) the folded absorbent sanitary articles 16 must be discarded. For this object, one or both of the folding lines 18, 20 may be equipped with reject systems. The reject systems may be located at the slowing devices 42 or the belt folding devices 22.

With reference to FIGS. 3a, 3b, 3c, 3d, 3e, the operating method of the apparatus 10 is as follows.

In a first step illustrated in FIG. 3a, the method involves forming an inlet array 14 formed by a plurality of absorbent sanitary articles 16 aligned with each other.

The absorbent sanitary articles 16 forming the inlet array 14 in an extended position and without packaging advance along the machine direction MD at the first speed V1.

Then, as illustrated schematically in FIG. 3b, the absorbent sanitary articles 16 coming from the inlet array 14 are routed alternately towards at least two folding lines 18, 20. In FIG. 3b and in the successive figures, the absorbent sanitary articles 16 are illustrated both in plan and in side view.

Subsequently, as shown schematically in FIG. 3c, in each of the folding lines 18, 20 the absorbent sanitary articles 16 are slowed down to a second speed V2 less than the first speed V1.

In each folding line 18, 20 the absorbent sanitary articles may be slowed down to the second speed V2 by respective rotating repitch devices 42.

The pitch between the absorbent sanitary articles 16 decreases proportionally to the decrease in speed. For example, if the speed V2 is half the speed V1, the pitch between the movable absorbent sanitary articles 16 at the speed V2 is equal to half the pitch between the same movable absorbent sanitary articles 16 at the speed V1.

In a possible embodiment, in the folding lines 18, 20 the absorbent sanitary articles 16 may advance at different speeds.

Then, as illustrated schematically in FIG. 3d, in each of the folding lines 18, 20 the absorbent sanitary articles 16 are folded around respective transverse axes while advancing at the second speed V2. As already described previously, in each of the folding lines the absorbent sanitary articles 16 may be folded by inserting them into folding channels 30, 32 formed between parallel branches of two belts 24, 26, 28. The absorbent sanitary articles 16 may be inserted into the folding channels 30, 32 by rotating folding blades 38, 40.

In each folding line 18, 20 the folded absorbent sanitary articles 16 leaving the respective belt folding devices 22 are picked up by respective outlet conveyors 54, 56 that feed the folded absorbent sanitary articles 16 into a common outlet array 58.

In the common outlet array 58 the absorbent sanitary articles 16 coming from the folding lines 18, 20 are aligned with each other in a single line.

As schematically illustrated in FIG. 3e, the folding lines 18, 20 feed respective folded absorbent sanitary articles 16 to the common outlet array 58 in phase with each other so that in the common outlet array 58 the folded absorbent sanitary articles 16 coming from the folding lines 18, 20 are alternated with each other.

In the case wherein two folding lines 18, 20 are provided, each folded absorbent sanitary article 16 coming from one folding line 18, 20 is arranged between two folded absorbent sanitary articles 16 coming from the other folding line 18, 20.

In a folding apparatus according to the prior art with a single folding line, the process of folding into three causes a gap to be created in the outlet array between consecutive folded absorbent sanitary articles. The folded absorbent sanitary articles spaced apart in this way are placed on a continuous packaging sheet on which, at the empty spaces between the consecutive articles, there would be an unwanted excess quantity of packaging material. In the prior art, to avoid this problem it is necessary to bring the folded absorbent sanitary articles closer together, slowing them down, in the outlet array.

In the solution according to the present invention, in the common outlet array 58 the empty spaces between the folded absorbent sanitary articles 16 coming from one of the folding lines 18, 20 may be filled by the folded absorbent sanitary articles 16 coming from the other folding line 18, 20.

In this way, in the common outlet array 58 the folded absorbent sanitary articles 16 are placed close together. This avoids unwanted empty spaces between folded absorbent sanitary articles 16. Thus, in the common outlet array 58 it is possible to maintain the same speed V2 that the folded absorbent sanitary articles 16 have at the outlet of the folding lines 18, 20.

The folded absorbent sanitary articles 16 obtained in accordance with the present invention may be packaged individually or in groups.

The outlet conveyors 54, 56 that receive the folded absorbent sanitary articles 16 from the respective belt folders 22 may be configured to selectively vary the speed of the individual folded absorbent sanitary articles 16.

The solution according to the present invention allows the folding of the absorbent sanitary articles to be carried out at a lower speed (for example halved) compared to the speed at which the absorbent sanitary articles leave at the end of the production machine. This allows a considerable reduction in the risk of damage to the absorbent sanitary articles.

Of course, the details of construction and the embodiments can be widely varied with respect to those described and illustrated, without thereby departing from the scope of the present invention as defined by the claims that follow.

The invention claimed is:

1. A method for folding absorbent sanitary articles, comprising:
   providing an inlet array formed by a plurality of absorbent sanitary articles, wherein in the inlet array the absorbent sanitary articles are unpackaged and advance along a machine direction at a first speed,
   routing the absorbent sanitary articles coming from said inlet array towards at least two folding lines,
   in each of said at least two folding lines, slowing down the absorbent sanitary articles at a respective second speed less than said first speed, wherein the at least two folding lines include a conveyor belt advancing at the second speed,
   in each of said at least two folding lines, folding said absorbent sanitary articles around respective transversal axes while said absorbent sanitary articles advance at said respective second speed, and
   feeding folded absorbent sanitary articles aligned together in a common outlet array.

2. The method of claim 1, wherein said second speed includes two second speeds that are different from each other; wherein said at least two folding lines includes two folding lines; wherein in one of said two folding lines, said absorbent sanitary articles advance at one of the two second speeds; and wherein in the other of said two folding lines said absorbent sanitary articles advance at the other of the two second speeds.

3. The method of claim 1, wherein said at least two folding lines feed respective folded absorbent sanitary articles towards said common outlet array in phase with each other in the machine direction, so that in said common outlet array the folded absorbent sanitary articles coming from a folding line of the at least two folding lines are alternated with folded absorbent sanitary articles coming from another folding line of the at least two folding lines.

4. The method of claim 1, wherein in each of said at least two folding lines, the absorbent sanitary articles are slowed down to the respective second speed by respective rotating repitch devices.

5. The method of claim 1, wherein in each of said at least two folding lines, the absorbent sanitary articles are folded by inserting the absorbent sanitary articles into folding channels formed between parallel branches of two belts.

6. The method of claim 1, wherein the speeds of individual folded absorbent sanitary articles at an exit of respective folding lines of the at least two folding lines are selectively controlled before feeding the individual folded absorbent sanitary articles into said common outlet array.

7. An apparatus for folding absorbent sanitary articles, comprising:
   an inlet conveyor configured to advance an inlet array formed by a plurality of absorbent sanitary articles along a machine direction at a first speed,
   at least two folding lines each comprising a slowing device configured to slow down the absorbent sanitary articles to a respective second speed less than said first speed, wherein the at least two folding lines include a conveyor belt advancing at the respective second speed, wherein said at least two folding lines are configured to fold said absorbent sanitary articles around respective transverse axes while said absorbent sanitary articles advance at said respective second speed, and a routing device configured to route the absorbent sanitary articles coming from said inlet array towards said at least two folding lines, wherein said at least two folding lines are configured to feed folded absorbent sanitary articles aligned with each other in a common outlet array.

8. The apparatus of claim 7, wherein said at least two folding lines are configured to feed respective folded absorbent sanitary articles to said common outlet array in phase with each other in the machine direction, so that in said common outlet array the folded absorbent sanitary articles coming from a folding line of the at least two folding lines are alternated with folded absorbent sanitary articles coming from another folding line of the at least two folding lines.

9. The apparatus of claim 7, wherein each of said at least two folding lines includes a rotary repitch device configured to slow down the absorbent sanitary articles to the respective second speed.

10. The apparatus of claim 7, wherein said at least two folding lines comprise respective outlet conveyors configured to selectively vary a speed of individual folded absorbent sanitary articles fed to said common outlet array.

* * * * *